(12) United States Patent
Law

(10) Patent No.: US 9,144,625 B2
(45) Date of Patent: Sep. 29, 2015

(54) CELLULOSE ETHYLSULFONATE-BASED ABSORBENT MATERIAL

(75) Inventor: Stephen Law, West Midlands (GB)

(73) Assignee: SPECIALITY FIBRES AND MATERIALS LTD., London (GB)

(*) Notice: Subject to any disclaimer, the term of this patent is extended or adjusted under 35 U.S.C. 154(b) by 445 days.

(21) Appl. No.: 13/131,653

(22) PCT Filed: Nov. 27, 2009

(86) PCT No.: PCT/GB2009/051608
§ 371 (c)(1),
(2), (4) Date: May 27, 2011

(87) PCT Pub. No.: WO2010/061225
PCT Pub. Date: Jun. 3, 2010

(65) Prior Publication Data
US 2011/0238025 A1    Sep. 29, 2011

Related U.S. Application Data

(63) Continuation-in-part of application No. 12/574,322, filed on Oct. 6, 2009.

(30) Foreign Application Priority Data

Nov. 27, 2008  (GB) .................................. 0821675.6
Dec. 11, 2008  (EP) .................................. 08171355

(51) Int. Cl.
*A61L 15/28* (2006.01)
*A61L 15/22* (2006.01)
*A61L 15/46* (2006.01)

(52) U.S. Cl.
CPC .............. *A61L 15/46* (2013.01); *A61L 15/28* (2013.01); *A61L 2300/104* (2013.01); *A61L 2300/206* (2013.01); *A61L 2300/404* (2013.01)

(58) Field of Classification Search
USPC .......................... 536/124; 604/367, 370, 374
See application file for complete search history.

(56) References Cited

U.S. PATENT DOCUMENTS

| | | | |
|---|---|---|---|
| 2,580,352 A | 12/1951 | Grassie | |
| 2,811,519 A * | 10/1957 | Touey | ............................ 536/90 |
| 4,200,557 A | 4/1980 | Chatterjee et al. | |
| 4,637,820 A | 1/1987 | Marini et al. | |
| 4,783,448 A | 11/1988 | Johansson | |
| 4,990,609 A * | 2/1991 | Herzog et al. | .................. 536/92 |
| 5,456,982 A | 10/1995 | Hansen et al. | |
| 5,703,225 A | 12/1997 | Shet et al. | |
| 5,840,769 A | 11/1998 | Kolter et al. | |
| 5,981,410 A | 11/1999 | Hansen et al. | |
| 5,986,087 A | 11/1999 | Schrell et al. | |
| 6,444,214 B1 | 9/2002 | Cole et al. | |
| 6,500,947 B1 | 12/2002 | West et al. | |
| 6,951,933 B2 | 10/2005 | West et al. | |
| 2004/0010215 A1 | 1/2004 | Gibbins et al. | |
| 2006/0142477 A1 | 6/2006 | Glasser et al. | |
| 2006/0142484 A1 | 6/2006 | Glasser et al. | |
| 2006/0142560 A1 | 6/2006 | Glasser et al. | |
| 2006/0286154 A1 | 12/2006 | Levy et al. | |
| 2008/0147026 A1 | 6/2008 | Qin et al. | |

FOREIGN PATENT DOCUMENTS

| | | |
|---|---|---|
| EP | 0210756 | 2/1987 |
| EP | 0511540 | 11/1992 |
| GB | 769799 | 3/1957 |
| GB | 813900 | 5/1959 |
| GB | 1207352 | 9/1970 |
| GB | 1503198 | 3/1978 |
| WO | WO 93/12768 | 7/1993 |
| WO | WO 01/43788 | 6/2001 |
| WO | WO 01/52911 | 7/2001 |
| WO | WO 0152911 A2 | 7/2001 |
| WO | WO 02/062320 | 8/2002 |
| WO | WO 2006/034249 | 3/2006 |
| WO | WO 2008/057267 | 5/2008 |
| WO | WO 2009/008557 | 1/2009 |
| WO | WO 2009/129244 | 10/2009 |

OTHER PUBLICATIONS

Cole et al., *Solvent-Spun Fibre—A new Member of the Cellulose Fibre Family*, Lenzinger Berichte—Heft 69 73-77 (1990).
Great Britain Search Report for GB 0821675.6 dated May 7, 2009 (2 pgs).
Timell, Tore, "Investigations on Cellulose Reactions . . . ", Svensk Papperstidning, vol. 51, 1948, pp. 254-258 (Abstract only) (1 pg).

(Continued)

*Primary Examiner* — Ganapathy Krishnan
(74) *Attorney, Agent, or Firm* — Stinson Leonard Street LLP

(57) ABSTRACT

This invention relates to absorbent materials useful in the manufacture of absorbent articles, in particular dressings for the advanced wound care market. The absorbent materials of the present invention are sulfonated polysaccharides, particularly water-insoluble cellulose alkyl sulfonates in which the cellulose is substituted by one type of alkyl sulfonate group. The invention also provides a process for the manufacture of such materials. The preferred cellulose alkyl sulfonate described herein is cellulose ethyl sulfonate. Reinforcing fibers and/or antimicrobial agents are optionally applied to the cellulose alkyl sulfonate.

17 Claims, 1 Drawing Sheet

(56) References Cited

OTHER PUBLICATIONS

Nakhoroshkov et al., "Explanation of the Cellulose Sulfoethylation Mechanism", Koksnes Kimija, No. 6, 1988, pp. 20-27 (Abstract only) (1 pg).

European Patent Office Search Report for EP 08171355.4 dated May 27, 2009 (9 pgs).
International Premliminary Report on Patentability for PCT/GB2009/051608 dated Mar. 1, 2011 (9 pgs).
International Search Report for PCT/GB2009/051608 dated Jun. 14, 2010 (5 pgs).

* cited by examiner

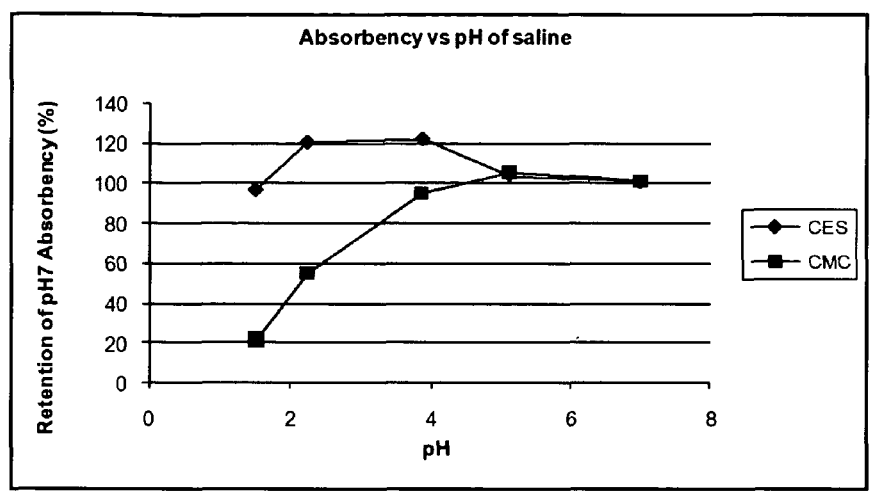

CELLULOSE ETHYLSULFONATE-BASED ABSORBENT MATERIAL

CROSS-REFERENCE TO RELATED APPLICATIONS

This application is a national phase application from PCT/GB2009/051608 filed on Nov. 27, 2009, which is based on and claims priority to Great Britain Patent Application 0821675.6, filed on Nov. 27, 2008, and European Patent Application No. 08171355.4, filed on Dec. 11, 2008, and U.S. patent application Ser. No. 12/574,322, filed on Oct. 6, 2009, all of which are hereby incorporated herein by reference.

BACKGROUND OF THE INVENTION

Absorbent fibers useful as components in advanced wound care dressings are known in the art, particularly fibers based on alginic acid, carboxymethylcellulose, and carboxymethylchitosan, and salts thereof.

Dressings based on fibers of alginic acid or its salts have good overall absorbency of wound fluid, but suffer from slow absorption due to the need to exchange multivalent ions binding the fibrous structure together with sodium ions present in wound fluid. Although this ion exchange renders the fibers swellable in ion-containing aqueous media, allowing significant absorption of fluid, the mechanical strength of the gelled fibers is compromised, and it is not routinely possible to remove a saturated dressing in one piece. Frequently, the dressing must be irrigated with saline to wash it away, and this can be traumatic for the patient.

Carboxymethyl cellulose fibers have also been used as the main component in advanced wound care dressings, and these too have significant absorptive capacity for wound fluid. Their advantage over alginate-type dressings is that absorption of fluid is virtually instantaneous since no ionic exchange is required to render the fibers gellable. In addition, those fibers based on a highly crystalline cellulose, such as lyocell, and in particular those described in EP0616650 and EP0680344, tend to retain a higher level of mechanical strength and therefore may be removed from the wound site in one piece. However the absorptive capacity of this class of material is strongly dependent on the pH of the wound fluid, reducing dramatically at acidic pH. This is a serious drawback since chronic wound fluid pH can range between 4 and 8 depending on the state of healing. Furthermore, it has been recognized that artificially lowering the pH of the wound environment may lead to improved healing outcomes. For instance, it has been found (Tsioras et al, article presented at 19th Annual Symposium on Advanced Wound Care, San Antonio, Tex., Apr. 30, 2006-May 3, 2006) that applying a wound dressing containing a pH adjusting cream of pH 2.8 decreased the time it took for the wound to close. In another study, burn wounds healed quicker when treated with fluid having a pH of 3.5 (Kaufman et al., Burns Incl Therm Inj, 12(2) 84-90 (1985)). Indeed, preparations are commercially available for use in conjunction with absorbent dressings to reduce the pH of the wound environment. For instance, CADESORB® available from Smith & Nephew has a pH of about 4.35.

It is desirable for an absorbent dressing to perform well at acidic pH, and preferably for it to perform well over a wide range of pH. Since absorbent dressings based on carboxymethylcellulose do not perform well in low pH environments, there is a need for an instantly gelling, absorptive dressing that continues to absorb to a good level at reduced pH.

It is desirable for absorbent fibers for use in absorbent dressings to be obtained from a renewable resource, to be inexpensive and also biodegradable. Hence, there is considerable interest in cellulose as a renewable and biodegradable source of absorbent material. U.S. southern pine fluff pulp is used as an absorbent material in the personal care industry. However, it is commonly used in conjunction with other absorbent materials, and commonly materials that are not renewable and biodegradable, for example acrylic acid polymers. The reason for this is that absorbed liquid is not effectively retained in materials that are made exclusively of cellulosic fibers.

The cellulose fiber can be modified by sulfonation, for example by substitution with an alkyl sulfonate at one or more of the hydroxyl groups on the anhydroglucose monomers that make up the cellulose backbone, forming ether linkages. Cellulose derivatives of this type are known as cellulose sulfonates or cellulose alkyl sulfonates.

Commercially available cellulose ethers are, as a rule, water-soluble compounds. In particular, cellulose ethyl sulfonate is known to be water-soluble.

Herzog et al., U.S. Pat. No. 4,990,609 describes cellulose ethyl sulfonates of high solution quality, which are prepared by addition to cellulose of an alkylating agent and subsequently addition of alkali. The process is compared to the two-stage process for the production of cellulose ethyl sulfonate described in SU757540.

Cellulose ether sulfonates have been modified further in order to produce water insoluble products. For instance Glasser et al., U.S. Published Patent Application No. 2006/0142560 refers to absorbent fibers based on mixed cellulose alkylsulfonates in which the cellulose is substituted by two different groups, an alkyl sulfonate and a hydroxyalkyl sulfonate, specifically ethyl sulfonate and 2-hydroxypropyl sulfonate. Water insolubility of the modified cellulose is believed to result from the presence of the 2-hydroxypropyl sulfonate group.

Shet et al., U.S. Pat. No. 5,703,225 refers to a water-insoluble sulfonated cellulose that is a hydroxy sulfonic cellulose in which both the sulfur atom of a sulfonic group and a hydroxyl group are directly attached to a carbon atom on the cellulose chain.

To be suitable for use in wound dressings, absorbent materials must retain their integrity and hence be water-insoluble. The principal disadvantage of the water insoluble cellulose alkyl sulfonates that have been developed for use as absorbent materials to date is the requirement for substitution of the cellulose with at least two different groups. Compared to substitution with a single substituent, additional reactants and additional processing steps are not desirable, and are likely to increase the cost of manufacture. Furthermore, as the cellulose is increasingly modified, benefits associated with the natural fiber, such as its biodegradability, may be impaired.

SUMMARY OF THE INVENTION

It has surprisingly been found that water-insoluble cellulose alkyl sulfonates may be prepared by the substitution of cellulose with only one type of alkyl sulfonate.

It will be clear to those skilled in the art that other polysaccharide substrates could be converted to an alkyl sulfonate derivative in accordance with the invention. For example, chitin and chitosan are natural polysaccharides based on D-glucosamine units, which have hydroxyl groups at positions at C3 and C5 where reaction substitution with alkyl sulfonate groups can take place. In addition, it is possible to substitute at the amine group in the C2 position, attaching the alkyl sulfonate via the nitrogen.

Thus, according to a first aspect of the invention, there is provided an absorbent article comprising as an absorbent material, a water-insoluble polysaccharide alkyl sulfonate, wherein the polysaccharide is substituted with one type of alkyl sulfonate.

The modified polysaccharides of the invention are highly advantageous for use as absorbent materials in wound dressings because they exhibit excellent absorption and retention of fluid while maintaining their integrity sufficiently to be removed from the wound site in one piece, without irrigation, and with minimum pain and shedding. As with carboxymethyl cellulose, absorption of fluid is virtually instantaneous since ionic exchange is not required for the fibers to become gellable. However, the water-insoluble polysaccharide alkyl sulfonates of the present invention are advantageous compared to carboxymethyl cellulose because the absorptive capacity may be affected to a lesser extent by changes in pH. Wound dressings containing these materials may continue to absorb to a good level at low pH.

In many embodiments of the absorbent articles according to the invention, the water-insoluble polysaccharide alkyl sulfonate is the only absorbent material present. Such embodiments do not contain other absorbent materials such as hydrogels, anion-exchange resins or combinations thereof.

The polysaccharide alkyl sulfonate may be used in the form of fibers. The fibers may be used in a wide range of lengths, eg a few mm, such as 2 mm or 5 mm, to several tens of mm, eg 100 mm, or more. However, for many applications the fibers are 20-50 mm in length. The fibers preferably have a linear density of in the range of 0.1 to 30 decitex, more preferably about 0.5 to 20 decitex, and most preferably 0.9 to 3 decitex.

When referring to the "absorbency" of a polysaccharide alkyl sulfonate we refer to the capacity of the polysaccharide alkyl sulfonate to take up fluid. In preferred embodiments where the polysaccharide ethyl sulfonate is a fiber, fluid is absorbed into the internal fiber structure and the fiber swells.

However, when measuring absorbency of an article of the present invention (comprising an polysaccharide alkyl sulfonate), we measure the overall absorptive capacity of the article to take up fluid, and this value will include the absorptive capacity directly attributable to the absorption of fluid by the individual fibers as well as absorption due to the open structure of the article. For example, fluids will be drawn into the air spaces or inter-fiber volumes between the fibers. Thus, the overall absorptive capacity is sensitive to the sizes and interconnectivity of the inter-fiber volumes within the fabric, and hence its method of manufacture.

For that reason, fibers may be useful as absorbent materials no matter what the chemical nature of the fiber material. Even fibrous materials made of non-absorbent polymers may exhibit some absorbency, because fluid is drawn into the inter-fiber volumes.

Measurement of the overall absorptive capacity of an article is a convenient and effective method of determining the effectiveness of the article as an absorbent material for applications such as wound dressings. Nevertheless, the advantages of the absorbent materials that are described in the present invention, compared to absorbent materials described in the prior art, are primarily due to the chemical nature and resulting absorbency of the materials used, and in particular the use of the water-insoluble polysaccharide alkyl sulfonate, wherein the polysaccharide is substituted with one type of alkyl sulfonate.

The polysaccharide alkyl sulfonate may be a cellulose alkyl sulfonate, and the following description refers primarily to such embodiments of the invention. It will be appreciated, however, that other polysaccharides may be utilized.

The alkyl moiety of the alkyl sulfonate substituent group is preferably a lower alkyl having 1 to 6 carbon atoms, preferably methyl, ethyl, propyl, or butyl. Preferably the alkyl moiety is not substituted by any other substituents, for example hydroxyl groups. The alkyl moiety may be branched or unbranched, and hence suitable propyl sulfonate substituents may be 1- or 2-methyl-ethylsulfonate. Butyl sulfonate substituents may be 2-ethyl-ethylsulfonate, 2,2-dimethyl-ethylsulfonate, or 1,2-dimethyl-ethylsulfonate. The alkyl sulfonate substituent group that is most preferred is ethyl sulfonate. The present invention is not intended to cover cellulose alkyl sulfonates having an alkyl sulfonate substituent group that is 2-hydroxypropyl sulfonate.

Thus, a preferred cellulose alkyl sulfonate of the present invention is cellulose ethyl sulfonate, where ethyl sulfonate or one of its salts is attached via one or more of the hydroxyl groups on the anhydroglucose units of the cellulose. The structure of one anhydroglucose unit substituted by one ethyl sulfonate group is depicted by formula (I)

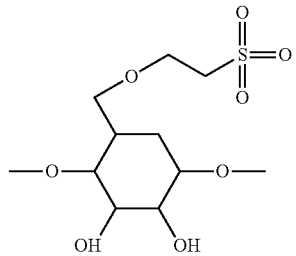

Formula (I) is not meant to depict the exact chemical structure of cellulose ethyl sulfonate prepared in accordance with the invention, because substitution can take place at any of the hydroxyl positions in the cellulose macromolecule, in any distribution up to the maximum degree of substitution that is possible.

The average degree of substitution refers to the mean number of hydroxyl positions substituted with an alkyl sulfonate substituent group, or put another way, the mean number of moles of alkyl sulfonate groups per mole of anhydroglucose unit in the cellulose polymer. The maximum degree of substitution is therefore 3, when the anhydroglucose unit is substituted at all three hydroxyl positions. The degree of substitution when an average of one hydroxyl group is substituted per anhydroglucose unit, as shown in Formula (I), is 1.

The functional properties of the cellulose alkyl sulfonates of the present invention depend on the degree of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

To be useful in an absorbent advanced wound dressing, the fibers of the absorbent material preferably have an absorbency of at least 8 grams per gram (g/g) of 0.9% saline solution, as measured by the method described below in Example 1. The fibers of the preferred cellulose alkyl sulfonates of the present invention have an absorbency (of 0.9% saline solution) of at least 8 g/g, more preferably at least 9 g/g, most preferably at least 10 g/g.

Another class of woundcare dressings, those which simply provide a non-adhesive wound contact layer, sometimes known as Tulle, do not require such a high level of absorbency since they may be used on wounds that exhibit a lower level of wound exudate generation, or a more absorbent layer is used on the top surface of the contact layer. However the key attribute of such contact layers is that they do not adhere to the wound bed. A fabric material comprising cellulose alkyl sulfonate fibers with a fabric absorbency greater than 2 g/g provides for a good contact layer dressing as the fibers absorb sufficient exudate, thus forming a gelled material to provide a non-adhesive surface. Thus, in another aspect, cellulose alkyl sulfonates of the present invention have an absorbency (of 0.9% saline solution) of greater than 2 g/g, 4 g/g, or 6 g/g.

It has been found that the average degree of substitution should preferably be less than 0.4 for the cellulose alkyl sulfonate to be substantially water-insoluble. By "substantially" is meant in this context that when the cellulose alkyl sulfonate is exposed to an excess of an aqueous medium it does not dissolve into solution, or at least that dissolution is so low as to have no significant effect on the properties of the polymer.

The average degree of substitution is preferably less than 0.4, more preferably less than 0.3. In some preferred embodiments of the invention, the average degree of substitution of the cellulose alkyl sulfonate is from about 0.05 to about 0.4, more preferably from about 0.1 to about 0.3.

Cellulose alkyl sulfonates with alkyl group having 2 to 6 carbon atoms according to the present invention can be formed by reaction of cellulose with an alkenyl sulfonate or one of its salts in the presence of a base, preferably an alkali metal hydroxide, either in aqueous or non-aqueous medium. Cellulose alkyl sulfonate with 1 carbon atom, i.e., cellulose methylsulfonate, can be formed by reaction with chloromethane sulfonic acid or one of its salts in the presence of a base, preferably an alkali metal hydroxide, either in aqueous or non-aqueous medium.

Alkalization and alkyl sulfonation (which in this case is an etherification step) may be carried out as a single step in which the base and alkenyl sulfonate or chloromethylsulfonate are added at the same time in one reaction vessel (a "one-pot" process). Alternatively, alkalization and alkyl sulfonation may be carried out in two separate reaction steps, treating the cellulose first with alkali and then alkyl sulfonating agent, or with alkyl sulfonating agent and then alkali.

Preferably alkalization and alkyl sulfonation (whether carried out in a single or separate reaction steps) are carried out in an aqueous medium. Most preferably alkalization and alkyl sulfonation are carried out in water. It is generally preferred to avoid the use of organic solvents, such as isopropanol, n-propanol, butanol, methanol, ethanol, acetone, dioxane, benzene, toluene, tetrahydrofuran, ethylene glycol and diethyl ether.

One-pot processes are often desirable because they can be easier and quicker, and by minimizing the number of reaction steps a higher yield may be obtained.

When the alkali and alkyl sulfonating agent are used simultaneously in a one-pot process, to produce a cellulose alkyl sulfonate of the present invention, the reaction rate is higher than that observed for the equivalent reaction in which alkalization and alkyl sulfonation are carried out in separate steps. As mentioned above, the greater the degree of substitution, the greater the absorbency of the cellulose alkyl sulfonate material. Thus, the reaction rate may be determined by measuring the time taken for the alkyl sulfonation reaction to yield a product having a particular degree of absorbency. In practice, it is not easy to stop a reaction at a specific absorbency level. Nevertheless, it is clear that a reaction taking 90 minutes to reach an absorbency of 14.2 g/g is significantly faster than one that takes 120 minutes to reach an absorbency of only 9.7 g/g.

The amount of water in the reaction mixture is also shown to affect the reaction rate. Lowering the water content in a reaction in which alkalization and alkyl sulfonation are carried out simultaneously results in a significant increase in reaction rate. Lowering the water content in the alkyl sulfonation step of a reaction in which alkalization and alkyl sulfonation are carried out separately increases the rate, but to a lesser extent.

A one-pot process would also be expected to minimize exposure of the cellulose to the base, therefore keeping the alkaline, oxidative degeneration of the cellulose to a minimum. It is necessary to minimize degeneration of the cellulose during processing in order to ensure that the modified cellulose is sufficiently strong to be useful as an absorbent material in a wound dressing, and indeed to maximize both the dry strength and the wet strength of the product.

However, it has been found that the strength of the fibers prepared by a one-pot process may be surprisingly and significantly weaker than fibers prepared by carrying out alkalization and alkyl sulfonation in separate steps, depending on the level of water used in the reaction mixture.

When higher levels of water are used in the reaction, the cellulose alkyl sulfonates produced by a one-pot process have a surprisingly low fiber strength compared to the cellulose alkyl sulfonates produced by the analogous two-step process. The fibers are too weak to be suitable for processing using normal non-woven textile processing methods. If the level of water used in the reaction is reduced, the reaction rate increases and also the fiber strength increases to a useable level. However, a certain amount of diluent is required to be practicable, particularly in wetting the cellulose and ensuring an even and complete reaction.

According to a further aspect of the invention, there is provided a process for the preparation of water-insoluble cellulose alkyl sulfonate comprising the simultaneous reaction of cellulose with an alkali and alkyl sulfonating agent, wherein the only solvent is water, and wherein the weight of water present in the reaction is less than 1070%, preferably less than 1050%, preferably less than 1030%, of the (dry) weight of the cellulose. Fiber absorbencies of about 15 g/g were achieved at 1027% water on a dry weight basis.

The weight of water present in the reaction is preferably more than 200%, preferably more than 300%, preferably more than 400% of the (dry) weight of the cellulose. Hence, the weight of water present in the reaction is preferably between 200 and 1070%, preferably between 300 and 1050%, and more preferably between 400 and 1030% of the (dry) weight of the cellulose. Most preferably, the weight of water present in the reaction is about 1027% of the (dry) weight of the cellulose.

According to a further aspect of the invention, there is provided a process for the preparation of a water-insoluble cellulose alkyl sulfonate, which process comprises the separate steps of:

(a) treating a cellulose with alkali;

(b) reacting the product of step (a) with an alkenyl sulfonate or its salt, or chloromethane sulfonic acid or its salt; and (c) isolating the product of step (b);

wherein the only solvent is water.

This two-step process is surprisingly beneficial when the level of water used in step (b) is more than 1070% of the (dry) weight of the cellulose.

In another aspect of the present invention, an absorbent article comprising the cellulose alkyl sulfonate fibers is provided. When fully hydrated, the absorbent article is substantially transparent. This is advantageous in wound care applications since the state of the underlying wound can be determined without removing the dressing.

In another aspect, the present invention is directed to an absorbent fabric article comprising cellulose alkyl sulfonate of the present invention which is reinforced with a reinforcing fiber blended or bonded to the water-insoluble polysaccharide alkyl sulfonate. The use of sheath/core bicomponent fibers is particularly advantageous because the sheath material melts at a lower temperature than the core so on bonding leaves a strong, unmelted core superstructure. In the present invention, it was found unexpectedly that when thermoplastic bicomponent fibers based on polyolefins (preferably a polypropylene core/polyethylene sheath) are used to reinforce cellulose ethyl sulfonate fibers, even up to a level of 20% by weight, the absorbency of the resultant fabric is not compromised by the substantially non-absorbent, hydrophobic reinforcing component. Moreover, using a reinforcing fiber having a lower linear density allows for a reduction in the weight amount of the fibers, resulting in increased transparency of the absorbent article.

In yet another aspect, the absorbent fabric articles comprising the cellulose alkyl sulfonate of the present invention exhibit an absorbency of at least 15 g/g using a sodium/calcium test solution formed by dissolving 16.6 g of NaCl and 0.74 g of CaCl dihydrate in 2 L of water. Absorbency is preferably not compromised using a reinforcing fiber, while wet strength is improved. Thus, the absorbency of the composite product comprising the cellulose alkyl sulfonate fibers and the reinforcing fibers is preferably at least 15, 16, 17, 18, 19, or 20 g/g using the sodium/calcium test solution. The wet strength of the composite product is preferably at least 1, 2, 3, 4, 5, or 6 N/cm/100 gsm (where gsm is grams per square centimeter) when using the sodium calcium test solution and Instron tensile testing machine as outlined in Example 9.

In still another aspect, one or more antimicrobial agents are applied to the polysaccharide alkyl sulfonate fibers and absorbent articles of the present invention. Preferred agents include silver and/or polyhexamethylene biguanide ("PHMB"). The weight of the silver cation in the product is preferably about 0.5 to 10 wt %, preferably about 0.5 to 5 wt %, preferably about 1 to 3 wt %, and still more preferably about 1.5 to 2.0 wt %. The weight of PHMB is preferably about 0.1 to 5%, preferably about 0.1 to 1%, and is preferably about 0.5 to 0.7 wt %.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DESCRIPTION OF THE DRAWINGS

FIG. 1 shows the absorbency of cellulose ethyl sulfonate ("CES") fibers of the present invention compared to carboxymethyl cellulose ("CMC") fibers as described in Example 8.

DETAILED DESCRIPTION OF THE INVENTION

Processes for preparing the cellulose alkyl sulfonates of the present invention were compared using 47% NaOH solution, 25% sodium vinylsulfonate solution, and different quantities of water in the alkyl sulfonation reaction.

When water was used at a level above 1070% of the (dry) weight of the cellulose, the reaction rate of the one-pot process was significantly higher, but the filament strength of the cellulose ethyl sulfonate product produced by the one-pot process was lower than the strength of the fiber produced by the two-step process with separate alkalization and alkyl sulfonation steps. Indeed, the filament strength of the product of the one-pot process was too low for the material to be effective for use, as intended, in wound dressing applications.

In the one-pot process for the preparation of water-insoluble cellulose alkyl sulfonate comprising the simultaneous reaction of cellulose with an alkali and alkyl sulfonating agent, the weight of water present in the reaction is less than 1070% of the (dry) weight of the cellulose, preferably less than 1050% by weight of the cellulose, and more preferably less than 1030% by weight of the cellulose.

Reducing the level of water in the second alkyl sulfonation step in the two-step process is shown to increase the reaction rate. However, it is not always practicable to carry out that reaction step using lower levels of water, as it becomes increasingly difficult to wet the cellulose as the volume of alkyl sulfonate reactant decreases. The weight of water present in the reaction is preferably more than 200%, more preferably more than 300%, more preferably more than 400% of the (dry) weight of the cellulose. In any case, when using lower levels of water in the reaction, the one-pot process is preferred.

At higher levels of water, the two-step process is most suitable for producing cellulose alkyl sulfonates of the present invention with adequate fiber strength. Preferably, the weight of water present in the alkyl sulfonation step is more than 1030% by (dry) weight of the cellulose, more preferably more than 1050% by weight of the cellulose, and most preferably more than 1070% by weight of the cellulose.

To be suitable for use in the present invention, the cellulose is preferably fibrous in nature. The cellulose fibers should have a high degree of crystallinity and total orientation in order that the fibers maintain sufficient strength after derivatization to be processed, and that the resulting material is strong enough for its intended use.

In particular, the use of alkali in the alkalization step can degrade the cellulose backbone, causing chain scission and a reduction in the degree of polymerization, thereby resulting in the fibers having a lower strength after derivatization. The dry strength of the derivatized fibers must be sufficient to enable processing into woven or nonwoven structures, and, to be useful as an absorbent material in a wound dressing, the wet strength of the material must be sufficient to allow removal from the site in one piece.

Fibrous celluloses with a high degree of crystallinity, that are particularly suitable for use in the invention, include cotton or regenerated cellulose fibers such as lyocell.

It will be clear to those skilled in the art that it is possible to sulfonate particulate cellulose such as pulp fibers, then dissolve the sulfonated cellulose in a suitable solvent, such as a lyocell solvent or an ionic liquid, and spin the sulfonated cellulose as fibers, or extrude the sulfonated cellulose as a film or other extrusion to produce the absorbent material of the invention. Furthermore, a blowing agent could be added to the solution in order to produce a foamed absorbent material.

The cellulose may be alkalized by treatment with a strong alkali, preferably an alkali metal hydroxide such as sodium hydroxide. A 47% sodium hydroxide solution has been found to be suitable. Generally, the higher the concentration of alkali and the higher the reaction temperature, the faster the rate of reaction. The strength of the reaction conditions should be balanced with the need to avoid degradation of the cellulose substrate. However, the level of degradation of the cellulose is considerably lower than might be expected under the relatively intense reaction conditions that are required for alkalization. When carrying out the two-step process, it may be beneficial to remove excess alkali before proceeding with second alkyl sulfonation step, e.g., by mechanically squeezing the alkalized fibers.

In the case of the alkyl sulfonation step (or etherification step) with 2 to 6 carbon atoms, the reaction involves the nucleophilic addition of the alkoxide ion to an alkenyl sulfonate, specifically α-alkenyl sulfonate or its salt. The α-alkenyl sulfonate is preferably a lower alkenyl sulfonate, in which the alkenyl moiety has 2 to 6 carbon atoms. Preferably the α-alkenyl sulfonate is vinyl sulfonate, allyl sulfonate (1-propenyl sulfonate), isopropenyl sulfonate (1-methylvinyl sulfonate), 1-butenyl sulfonate, 1-methyl allyl sulfonate (1-methyl-1-propenyl sulfonate) or 2 methylallyl sulfonate (2-methyl-1-propenyl sulfonate). In a particularly preferred embodiment, the α-alkenyl sulfonate is vinyl sulfonate, more preferably the sodium salt of vinyl sulfonate, and hence the cellulose alkyl sulfonate product is cellulose ethyl sulfonate.

The sodium salt of vinyl sulfonate is commercially available as an approximately 30% aqueous solution. It may be brought into contact with the cellulose or alkalized cellulose by methods known in the art, for instance spraying onto the cellulose, or mixing using stirrers. The conversion to cellulose alkyl sulfonate can take place at any temperature up to the boiling point of the reaction mixture, or beyond it if a pressurized system is used. The rate of reaction is increased if the reaction stage is carried out at elevated temperature. The preferred range is 30-95° C. to give a useful degree of substitution in an economic time. Further, fresh charges of reactant can be introduced at any time throughout the reaction. The degree of substitution can be controlled by control of reaction temperature and, in particular, by control of the reaction time.

Vinyl sulfonate is thought to be less hazardous than some of the halogenated reactants, particularly chlorinated reactants, which are typically used to prepare the absorbent materials currently available for use in wound care products. Certainly, chloroacetic acid, used in the manufacture of carboxymethyl cellulose, is a potentially dangerous alkylating agent. Its use during the manufacturing process is undesirable, and retention of any residual chloroacetic acid in the absorbent product may be harmful, at the least causing skin irritation. The use of only one type of alkyl sulfonate also presents potential advantages in terms of safety and removal of residual reactant compared to other water-insoluble cellulose alkyl sulfonates that are known, in which the cellulose is substituted with more than one type of alkyl sulfonate, if only because of the relative simplicity of the chemistry.

After the reaction has proceeded to the desired extent, the reaction can be stopped by neutralizing the reaction mixture, i.e., reducing the pH to approximately neutral by addition of acid. The acid may be any common mineral or organic acid such as hydrochloric or acetic acid, respectively. The cellulose alkyl sulfonate product can then be washed free of by-products and impurities by employing washing stages known in the art. Such stages include washing with water, organic liquids, or mixtures thereof. Particularly useful are mixtures of a lower alcohol and water. Washing efficiency can be enhanced by washing at elevated temperature. After washing, it may be desirable to apply a processing aid, such as glycerol, as is common practice in the production of, for example, cellulose film (cellophane). This can be achieved by methods known in the art, such as dipping, spraying etc.

Finally the derivatized cellulose article should be dried to remove residual liquid from the previous stages. Drying can be carried out by methods known in the art such as forced air drying, radiant heat drying etc.

The absorbent materials of the present invention exhibit instant gelling in aqueous media, good absorbency and, crucially, good retention of absorbency in an acidic environment. This renders them ideal for use as an absorbent wound dressing, or as part of an absorbent dressing. They are particularly useful for wounds with moderate to high levels of exudates, and for flat or cavity wounds of this type. Typical examples include pressure sores and leg ulcers.

The use of the absorbent materials of the present invention is not limited to wound care products, and they are expected to be useful for many other applications. Their absorbent properties, biodegradability, and the fact that cellulose is a renewable material, mean that the cellulose alkyl sulfonates of the invention are also particularly desirable for use in the personal care sector, particularly for disposable sanitary articles such as nappies (diapers), disposable nappies and training pants, feminine care products, e.g., tampons, sanitary towels, or napkins and pant liners, and incontinence products. The simplicity of the chemistry and the availability of the reactants enable the cost of manufacture of such articles to be kept advantageously low.

Other medical products are envisaged, for example, surgical and dental sponges. The materials could also be useful in packaging, for example as absorbent pads in food containers.

The cellulose alkyl sulfonates of the present invention may be processed according to known methods into a wide variety of forms, depending on their intended use. The manner in which the derivative cellulose is processed has a significant effect on the properties of the final product, particularly the strength, gelling time, and absorbency. Preferred cellulose alkyl sulfonate products for use in wound care articles are carded, needle-bonded nonwovens.

The cellulose alkyl sulfonates may be combined with one or more reinforcing fibers as generally set forth in Hansen, U.S. Pat. No. 5,981,410 titled "Cellulose-Binding Fibres"; Stengaard et al., U.S. Pat. No. 6,811,716 titled "Polyolefin Fibers and Method for the Production Thereof"; Jensen et al., U.S. Pat. No. 5,958,806 titled "Cardable Hydrophobic Polyolefin Fibres Comprising Cationic Spin Finishes;" all of which are incorporated by reference. Preferred reinforcing fibers are thermoplastic bicomponent fibers, most preferably having a polyolefin component. Thus, the fibers preferably comprise a polyolefin-containing polymeric material of which the largest part (by weight) consists of homo- or copolymers of monoolefins such as ethylene, propylene, 1-butene, 4-methyl-1-pentene, etc. Examples of such polymers are isotactic or syndiotactic polypropylene, polyethylenes of different densities, such as high density polyethylene, low density polyethylene, and linear low density polyethylene and blends of the same. The polymeric material may be mixed with other non-polyolefin polymers such as polyamide or polyester, provided that polyolefins still constitute the largest part of the composition. The melts used to produce the polyolefin-containing fibers may also contain various conventional fiber additives, such as calcium stearate, antioxidants, process stabilizers, compatibilizers, and pigments. Methods for applying the thermoplastic bicomponent fibers are described in EP0740554; EP0171806; Ejima et al., U.S. Pat. No. 5,456,982; Davies, U.S. Pat. No. 4,189,338; Davies, U.S. Pat. No. 3,511,747; and Reitboeck et al., U.S. Pat. No. 3,597,731, which are incorporated by reference.

The thermoplastic bicomponent fibers may be of the sheath-core type with the core being located either eccentrically (off-center) or concentrically (substantially in the center), or of the side-by-side type, in which each of the two components typically has a semi-circle cross section. Bicomponent fibers having irregular fiber profiles are also contemplated, e.g., an oval, ellipse, delta, star, multilobal, or other irregular cross section, as well as splittable fibers. The bicomponent fibers will typically have a high melting and low melting polyolefin component which comprise, respectively, polypropylene/polyethylene (the polyethylene comprising HDPE, LDPE, and/or LLDPE), high density polyethylene/linear low density polyethylene, polypropylene random copolymer/polyethylene, or polypropylene/polypropylene random copolymer. Preferred thermoplastic bicomponent fibers are commercially available from Fiber Visions (Athens, Ga.). Suitable thermoplastic bicomponent fibers comprise 30, 25, 20, 18, 16, 14, 12, 10, 8, 6, or 4 wt % or any range there between of the composite absorbent article. The thermoplastic bicomponent fibers preferably have a linear density of about 1.7, 1.9, 2.1, 2.3, 2.4, 2.6, 2.8, 3.0, 3.2, 3.4, 3.8, 4.0, 4.2, 4.4, 4.6, 4.8, 5.0 decitex up to 16.7 decitex or any range therebetween. However, it has been surprisingly discovered that when high-density fibers (e.g., 4.0 decitex) are incorporated into the absorbent article comprising the cellulose alkyl sulfonate at high levels (e.g., about 20%), the absorbency of the article is not compromised. Moreover, using a reinforcing fiber having a lower linear density allows for a reduction in the weight amount of the fibers, resulting in increased transparency. Thus, in one aspect, the thermoplastic bicomponent fibers preferably comprise about 10 to 30 wt % (more preferably about 10 to 20%, and still more preferably about 10 to 13%) of the absorbent article and have a linear density of about 1.7 to 4.0 decitex (more preferably about 1.7 to 1.9 decitex). The temperature used to fuse the fibers together is typically in the range of 90 to 162° C., preferably about 120 to 125° C.

In another aspect, the reinforcing fibers comprise lyocell fibers. These fibers generally comprise a cellulose obtained by an organic solvent spinning process. Preferably, the lyocell fiber is generated from cellulose fibers using various amine oxides as solvents. In particular, N-methylmorpholine-N-oxide ("NMNO") with water (about 12%) proves to be a particularly useful solvent. Examples of processes for preparing lyocell fibers are described in McCorsley et al., U.S. Pat. Nos. 4,142,913; 4,144,080; 4,211,574; 4,246,221; and 4,416,698, and others. Jurkovic et al., U.S. Pat. No. 5,252,284 and Michels et al., U.S. Pat. No. 5,417,909 deal especially with the geometry of extrusion nozzles for spinning cellulose dissolved in NMMO. Brandner et al., U.S. Pat. No. 4,426,228, is exemplary of a considerable number of patents that disclose the use of various compounds to act as stabilizers in order to prevent cellulose and/or solvent degradation in the heated NMMO solution. Franks et al., U.S. Pat. Nos. 4,145,532 and 4,196,282, deal with the difficulties of dissolving cellulose in amine oxide solvents and of achieving higher concentrations of cellulose. All of these patents are incorporated herein by reference. One lyocell product produced by Lenzing is presently commercially available as TENCEL® fiber. The methods for including these cellulose fibers into nonwoven structures to aid in integrity of the product is well known, see, e.g., GB1207352, which is incorporated by reference. In one aspect, the lyocell fibers comprise 26, 24, 22, 20, 18, 16, 14, 12, 10, 8, 6, or 4 wt % or any range therebetween of the composite absorbent article. The lyocell fibers preferably have a linear density of about 0.7, 0.9, 1.1, 1.3, 1.5, 1.7, 1.9, 2.1, 2.3, 2.4, 2.6, 2.8, 3.0, 3.2, 3.4, 3.8, 4.0, 4.2, 4.4, 4.6, 4.8, 5.0, 10, 15, 20, 25, up to 30 decitex or any range therebetween. As shown in the examples below, it has been surprisingly discovered that when low density fibers (e.g., about 1.2 to 1.6 decitex) are incorporated into the composite absorbent article at high levels (e.g., about 10 to 30 wt %, preferably about 10 to 20 wt %), the wet strength is improved while absorbency is not compromised. In a particularly preferred embodiment TENCEL® fibers are incorporated at about 15 to 20 wt %, eg 20 wt %, into cellulose ethyl sulfonate nonwoven materials.

In still another aspect, one or more antimicrobial agents are applied to the cellulose alkyl sulfonate of the present invention. Preferred agents include silver and/or polyhexamethylene biguanide ("PHMB").

The invention will now be illustrated by the following non-limiting examples.

Example 1

Method for Determination of the Free Absorbency of Fibers

The fiber was cut into a 2-3 mm flock, and 0.5 g of cut fiber was placed in a 100 ml screw-top jar. 50 ml of test liquid (e.g., 0.9% saline, typically used to simulate the ionic strength of wound fluid) was added, and the jar shaken for 30 seconds to disperse the flock. The dispersion was then filtered through a 47 mm Buchner funnel fitted with a 42.5 mm diameter Whatman No. 4 filter paper, using a vacuum pump, with vacuum set to be greater than 0.8 bar for one minute. Then the fiber dispersion was removed and weighed. Fiber free absorbency was calculated using the following formula:

$$\text{absorbency}(g/g) = \left[\frac{\text{wet\_dispersion\_weight}(g)}{\text{dry\_flock\_weight}(g)}\right] - 1$$

Example 2

Method for Determination of Breaking Tenacity and Elongation of Single Filaments Tenacity and elongation at break of dry, single filaments was carried out using a tensile testing machine, fitted with appropriate jaws for gripping single filaments and load cell of the appropriate range.

The samples were conditioned for at least four hours and were tested in the standard atmosphere for testing textiles (20±2° C. and 65±2% relative humidity).

The machine was balanced and calibrated according to the manufacturer's instructions. Filaments were taken at random from different parts of the sample. The linear density of the filament was measured by an appropriate technique such the Vibraskop method. The filament was then placed between the jaws of the tensile testing machine and the test started. The following conditions were used:

Test length: 20 mm
Load range: 0-10 cN
Cross-head speed: 10 mm/minute
Chart speed (when applicable): 10-20 mm/minute
Number of tests: 10

After rupture, the crosshead was returned, and the broken ends of filament were checked and removed from the jaws. A note was made if the number of jaw breaks exceeded 10%.

The breaking load (cN) and the breaking extension (%) of each filament was usually printed out together with the statistics. In the case of individual breaking loads being printed out, individual tenacity results or a mean tenacity were calculated by hand, as follows:

$$\text{mean tenacity}(cN/\text{tex}) = \frac{\text{mean breaking load in } cN \times 10}{\text{mean linear density in dtex}}$$

Example 3

Preparation of Cellulose Ethyl Sulfonate Using a Two-Step Process

A 3 g sample of lyocell tow, known under the tradename TENCEL® (manufactured by Lenzing), was immersed in aqueous 47% sodium hydroxide for 25 minutes at 25° C. Excess sodium hydroxide was then removed by squeezing. Then 25 ml 30% sodium vinyl sulfonate solution (Fluka Chemicals) was added to the fiber and heated at 91° C. for 90 minutes. After this time the reaction mixture was neutralized to pH 7 by adding glacial acetic acid dropwise. Then the excess liquid was squeezed from the fiber, and the fiber was washed twice in a mixture of industrial methylated spirit ("IMS") and water (80:20 v/v). After drying to constant weight at 60° C., the fiber was tested for absorbency.

Using the method outlined in Example 1, and an aqueous solution of 0.9% NaCl as the test liquid, a fiber free absorbency value of 11.1 g/g was achieved.

Example 4

Preparation of Cellulose Ethyl Sulfonate Using a Two-Step Process (SFM006/69)

A 2.5 g sample of TENCEL® fiber was immersed in 47% sodium hydroxide for 30 minutes at 20° C., after which excess liquid was removed by squeezing. 21 ml sodium vinyl sulfonate (30% aqueous solution) was poured over the fiber. The vessel containing fiber and reactant was then heated at 83° C. for two hours, after which time the sample was neutralized by the dropwise addition of glacial acetic acid until a pH of 7 was reached. The excess liquid was then squeezed from the fiber, and the fiber was washed twice with IMS/water (80:20 v/v), and finally in 100% IMS. After drying to constant weight at 60° C., the fiber was tested for absorbency according to the method in Example 1, using 0.9% aqueous NaCl as the test liquid. A fiber free absorbency value of 9.7 g/g was obtained.

Example 5

Preparation of Cellulose Ethyl Sulfonate Using a One-Pot Process with High Water Content 3 g TENCEL® fiber was immersed in a mixture of 10 ml 47% NaOH and 25 ml 30% sodium vinylsulfonate solution, and heated for 75 minutes at 83° C. The reaction mixture was then neutralized by addition of acetic acid, after which the fiber was removed and washed in a mixture of IMS/water (80:20 v/v), and finally in 100% IMS. Drying was carried out at 60° C.

Using the method outlined in Example 1, and an aqueous solution of 0.9% NaCl as the absorbent test liquid, a fiber free absorbency value of 6.6 g/g was achieved. The fibers were visibly weaker than the fibers of Example 6, despite having a lower degree of substitution, as evidenced by the lower absorbency value.

Example 6

Preparation of Cellulose Ethyl Sulfonate Using a One-Pot Process with Low Water Content (SFM006/145a)

3 g TENCEL® fiber was immersed in a mixture of 13 ml 30% sodium vinylsulfonate solution and 10 ml 47% NaOH solution, and heated for 70 minutes at 83° C. The reaction mixture was then neutralized by addition of acetic acid, after which the fiber was removed and washed in a mixture of IMS/water (80:20 v/v), and finally in 100% IMS. Drying was carried out at 60° C.

Using the method outlined in Example 1, and an aqueous solution of 0.9% NaCl as the test liquid, a fiber free absorbency value of 11.9 g/g was achieved.

Example 7

Comparative Absorbency Test for Underivatized Cellulose

TENCEL® fiber from the same batch used as the starting material for Examples 3 and 4 was subjected to the absorbency test outlined in Example 1, using 0.9% aqueous NaCl as the absorbent test liquid. A fiber free absorbency value of 0.9 g/g was obtained.

Example 8

Comparison of the Absorbency at Low pH of Cellulose Ethyl Sulfonate Fibers of the Present Invention with Carboxymethyl Cellulose Fibers of the Prior Art The absorbency of carboxymethyl cellulose (CMC) fibers made according to the teachings in EP 0616650 was measured according to the method of Example 1 using 0.9% saline solution as absorbing liquid. The pH of the saline was then reduced successively by addition of 37% HCl and the absorbency measured again at each pH.

Cellulose ethyl sulfonate fibers were produced according to the present invention from lyocell fiber, and their absorbency measured in the same way at a range of pH values.

The results are shown graphically in FIG. 1. It is clear that cellulose ethyl sulfonate fiber of the invention retains significantly more of its absorbency at low pH where wound healing is believed to be enhanced.

Example 9

20% by Weight 4.0 Decitex Bicomponent Fiber-Reinforced Cellulose Ethyl Sulfonate Fabric In this example, cellulose ethyl sulfonate fiber made according to the present invention was cut to 50 mm staple and blended in a 20% by weight proportion with 4.0 decitex 40 mm staple bicomponent fiber (ES-LOWMELT™ manufactured by Fiber Visions) through a sample card. The resulting web was needlebonded, and then thermally bonded by heating in a recirculating oven set at 125° C. for 10 minutes. Comparative cellulose ethyl sulfonate fabric containing no reinforcing fiber was manufactured in a similar manner, without a thermal bonding step.

The wet strength was measured by cutting test specimens 2.5 cm wide×10 cm long from the fabric. The sample was mounted in an Instron 3343 tensile testing machine to give a gauge length 5 cm. The sample was then wetted with 2.5 ml of solution A (sodium/calcium solution), left for one minute, and then tested at 100 mm/min. The sodium/calcium Solution A is formed by dissolving 16.6 g of NaCl and 0.74 g of CaCl dihydrate in 2 L of water.

The clarity was measured subjectively by placing beneath a gelled (0.9% saline hydrated) sample printed bold type face 12 pt Times New Roman and subjectively scoring the clarity from 0 (completely opaque, typeface not visible) to 10 (completely clear, undistorted typeface).

The absorbency was measured by weighing a 5 cm×5 cm square of sample material ($W^1$). Next, the sample was placed in Solution A at 37° C. for 30 minutes in a petri-dish. Then the square was lifted out of the petri-dish by holding the square by one corner, and the sample was allowed to drain for 30 seconds. The sample was then reweighed to obtain the end weight ($W_2$). The fabric absorbency is given by $(W_2-W_1)/W_1$.

TABLE 2

Summary of Test Results

| | Fabric Absorbency (g/g) | Wet strength (N/cm/100 gsm) | Clarity |
|---|---|---|---|
| CES Fabric | 15.9 | 0.6 | 9 |
| 20% 4.0 decitex bicomponent-reinforced fabric | 19.7 | 5.1 | 3 |

Example 10

10% by Weight 1.7 Decitex Bicomponent Fiber-Reinforced Cellulose Ethyl Sulfonate Fabric Cellulose ethyl sulfonate fabric prepared in accordance with the present invention containing 10% by weight 1.7 decitex 40 mm staple bicomponent fiber (ES-CURE™ manufactured by Fiber Visions) was manufactured in a similar manner to Example 9, except the thermal bonding step was conducted at 135° C., due to the higher melting sheath component. A fabric containing 10% 4.0 decitex ES-LOW MELT™ was also produced as in Example 9. The following table shows the results:

TABLE 3

Test Results

| | Wet strength (N/cm/100 gsm) | Clarity |
|---|---|---|
| 10% 1.7 decitex bicomponent-reinforced fabric | 2.1 | 6 |
| 10% 4.0 decitex bicomponent-reinforced fabric | 0.6 | 6 |

Example 11

20% by Weight 1.4 Decitex Lyocell-Reinforced Cellulose Ethyl Sulfonate Fabric

In this example, TENCEL® fibers were incorporated at a level of 20% by weight into cellulose ethyl sulfonate nonwoven materials. It was found that wet strength is improved significantly, while absorbency is little compromised. Cellulose ethyl sulfonate fiber in accordance with the present invention was cut to 50 mm staple and blended in a 20% by weight proportion with 1.4 decitex 50 mm staple TENCEL® fiber (manufactured by Lenzing AG) through a sample card. The resulting web was needlebonded. The following table shows the results:

TABLE 4

Test Results

| | Strength (N/cm/100 gsm) | Clarity | Fabric absorbency (g/g) |
|---|---|---|---|
| Unreinforced cellulose ethyl sulfonate fabric | 0.4 | 8 | 19.4 |
| TENCEL ® reinforced cellulose ethyl sulfonate fabric | 3.3 | 5 | 18.8 |

The strength, clarity, and absorbency of the fabric was determined as set forth in Example 9.

Example 12

Silver Alginate Fiber Blend Process

This example describes a blend of silver alginate fibers with cellulose ethyl sulfonate fibers using the techniques as generally set forth in WO 02/24240, which is incorporated by reference.

Calcium alginate fibers containing approximately 24% by weight silver were manufactured by immersing calcium alginate fibers in a mixture of water/acetone/silver nitrate, followed by washing in acetone/water and finally acetone before drying the fibers at 50° C. These fibers were cut to 50 mm staple and blended with cellulose ethyl sulfonate staple fibers in such a ratio to give approximately 1.5% silver on weight of dressing, then the blend was carded and needle-bonded to give approximately 100 gsm needled fabric. The fabric had an off-white color on prolonged exposure to light.

In a surface antimicrobial efficacy test known as Qualiscreen, the dressing was found to be antimicrobial, i.e., inhibited formation of greater than 99.9% of daughter cells (methicillin resistant *Staphylococcus aureus*).

Example 13

PHMB Cellulose Ethyl Sulfonate

In this example, a PHMB-loaded cellulose ethyl sulfonate fabric was produced by a spray method using a 20% aqueous solution of PHMB to give 0.6% PHMB by weight on dressing. A sample of the dressing was subjected to the "milk test." The dressing remained antimicrobial for 72 hours, while the control sample became populated with microbes after 24 hours.

Example 14

Low Gel Non-Adherent Contact Layer Dressing

Cellulose ethylsulphonate fibers with a fiber absorbency of 4.7 g/g as measured by the method in Example 1 were cut to 50 mm staple, then carded and needled to give a fabric. The absorbency of this fabric was measured by weighing a 5 cm×5 cm square of sample material ($W^1$). Next, the sample was placed in Solution A (sodium/calcium solution) at 37° C. for 30 minutes in a petri-dish. Then the square was lifted out of the petri-dish by holding the square by one corner, and the sample was allowed to drain for 30 seconds, then the sample was reweighed ($W_2$). The fabric absorbency is given by ($W_2$−$W_1$)/$W_1$.

The wet strength was measured by cutting test specimens 2.5 cm wide×10 cm long from the fabric. The sample was mounted in an Instron 3343 tensile testing machine to give a gauge length 5 cm. The sample was then wetted with 2.5 ml of solution A (sodium/calcium solution), left for one minute, and then tested at 100 mm/min.

A highly absorbent fabric from Example 11, prepared from cellulose ethylsulphonate fibers with a fiber free absorbency of 12.9 g/g served as a comparison. The absorbency and tensile strength results are shown in the table below:

TABLE 5

| | Strength (N/cm/100 gsm) | Fabric Absorbency (g/g) |
|---|---|---|
| Low gel non-adherent contact layer cellulose ethylsulphonate fabric | 1.32 | 16.8 |
| Highly absorbent cellulose ethylsulphonate fabric (Example 11) -- unreinforced | 0.4 | 19.4 |

It can be seen that absorbency is compromised in the case of the contact layer fabric, but wet strength is significantly improved. Furthermore the contact layer fabric exhibited a slippery feel suggesting a low adherence to skin.

Example 15

Chitosan Ethyl Sulfonate 3 g chitosan fiber was immersed in 40 ml 47% NaOH solution for 25 minutes at 25° C., after which excess liquor was removed by squeezing. 25 ml vinylsulfonate (30% aqueous solution) was poured over the fiber and heated at 83° C. for 120 minutes. The sample was then neutralised by addition of acetic acid, then washed in successive mixtures of IMS/water (80/20 v/v), and finally in 100% IMS. After drying at 60° C. to constant weight the fiber was tested for absorbency by the method outlined in Example 1 using 0.9% saline solution. A value of 3.7 g/g was obtained.

It is expected that absorbency may be improved with some optimisation of the reaction conditions. For example, by increasing the concentration of the NaOH solution and/or by using a higher concentration of vinyl sulfonate (eg 35% aqueous solution).

From the foregoing it will be seen that this invention is one well adapted to attain all ends and objectives hereinabove set forth, together with the other advantages which are obvious and which are inherent to the invention. Since many possible embodiments may be made of the invention without departing from the scope thereof, it is to be understood that all matters herein set forth or shown in the accompanying drawing are to be interpreted as illustrative, and not in a limiting sense. While specific embodiments have been shown and discussed, various modifications may, of course, be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A process for the preparation of water-insoluble cellulose alkyl sulfonate comprising simultaneously reacting solvent spun cellulose with an alkali and an alkenyl sulfonate or its salt, and wherein an amount of water present in the reaction is less than 1030% by weight of the cellulose and wherein there is no organic solvent present in the reaction.

2. The process of claim 1, wherein the weight of water present in the reaction is less than 800% by weight of the cellulose.

3. The process of claim 1, wherein the weight of water present in the reaction is less than 700% by weight of the cellulose.

4. The process of claim 1, wherein the weight of the water present in the reaction is less than 650% by weight of the cellulose.

5. The process of claim 1, wherein the alkenyl sulfonate is an α-alkenyl sulfonate.

6. The process of claim 5, wherein the α-alkenyl sulfonate is a lower alkenyl sulfonate.

7. The process of claim 1, wherein the alkenyl sulfonate is selected from the group consisting of vinyl sulfonate, allyl sulfonate, isopropenyl sulfonate, 1-butenyl sulfonate, 1-methyl allyl sulfonate, and 2-methylallyl sulfonate.

8. The process of claim 1 wherein the alkenyl sulfonate is vinyl sulfonate.

9. A process for the preparation of a water-insoluble cellulose alkyl sulfonate comprising the steps of:
   a. treating solvent spun cellulose with alkali;
   b. reacting the product of step (a) with an alkenyl sulfonate or its salts or chloromethane sulfonic acid or one of its salts in a medium that contains no organic solvent; and
   c. isolating the product of step (b).

10. The process of claim 9, wherein an amount of water present in step (b) is more than 650% by weight of the cellulose.

11. The process of claim 9, wherein the weight of the water present in step (b) is less than 750% by weight of the cellulose.

12. The process of claim 9, wherein the alkenyl sulfonate is an α-alkenyl sulfonate.

13. The process of claim 9, wherein the α-alkenyl sulfonate is a lower alkenyl sulfonate.

14. The process of claim 9, wherein the alkenyl sulfonate is selected from the group consisting of vinyl sulfonate, allyl sulfonate, isopropenyl sulfonate, 1-butenyl sulfonate, 1-methyl allyl sulfonate, and 2-methylallyl sulfonate.

15. The process of claim 9, wherein the alkenyl sulfonate is vinyl sulfonate.

16. The process of claim 9 further comprising the step of (d) drying the product of step (c).

17. The process of claim 9 wherein said alkali is sodium hydroxide.

* * * * *